United States Patent [19]

Kapin et al.

[11] Patent Number: 6,020,352

[45] Date of Patent: Feb. 1, 2000

[54] TREATMENT OF ISCHEMIC DISORDERS OF THE RETINA AND OPTIC NERVE HEAD

[75] Inventors: Michael A. Kapin, Arlington; Louis Desantis, Jr., Forth Worth, both of Tex.; Bernard Scatton, Villebon sur Yvette; Salomon Langer, Paris, both of France

[73] Assignee: Synthelabo, France

[21] Appl. No.: 08/972,833

[22] Filed: Nov. 18, 1997

Related U.S. Application Data

[63] Continuation of application No. 08/582,003, Jan. 2, 1996, abandoned.

[51] Int. Cl.$^7$ .................................................. A61K 31/445
[52] U.S. Cl. ............................................ 514/371; 514/912
[58] Field of Search ...................................... 514/317, 913

[56] References Cited

U.S. PATENT DOCUMENTS 4,690,931  9/1987  Wick et al. .............................. 514/317

FOREIGN PATENT DOCUMENTS

WO 94/13275   6/1994   WIPO .

OTHER PUBLICATIONS

Embase Abstract of L'angiosclerose, Oculaire 1977. Ardouin et al.

Cornand, et al., *Mediterr. Med.*, "Notre expérience du tartrate d'ifenprodil (Validex) en ophthalmologie," 7(191): 105–107, May 2, 1979.

Crampinchi, et al., *Bull. Mem. Soc. Fr. Ophthalm.*, "Traitement par injections répétées de vasodilatateurs des névrites optiques alcoolo–nicotiniques," 89:339–341, 1977.

Morgan, R., *Can. J. Ophthalmol.*, "Open–angle glaucoma: An epidemiologist's view," 7(1):75–79, 1972.

Zeevalk, et al., *Brain Res.*, "Action of the anti–ischemic agent ifenprodil on N–methyl–D–aspartate and kainate–mediated excitotoxicity," 522(1):135–139, 1990.

Kapin, et al., *Soc. Neurisci. Abstr.*, "Protective effect of the polyamine antagonist, eliprodil hydrochloride in retina subjected to an excitotoxic–or ischemic insult," 22(1–3):1279, 1996.

David, P., et al., "Involvement of excitatory neurotransmitters in the damage produced in chick embryo retinas by anoxia and extracellular high potassium," *Exp. Eye Res.*, 46: 657–662 (1988).

Massey, S., "Cell types using glutamate as a neurotransmitter in the vertebrate retina," *Progress in Retinal Research*, 9:339–425 (1990).

Miller, R. F. and M. M. Slaughter, "Excitatory amino acid receptors in the vertebrate retina," *Retinal Transmitters and Modulators*, II:123–160 (1985).

Benveniste, H. et al., "Elevation of the extracellular concentrations of glutamate and aspartate in rat hippocampus during transient cerebral ischemia monitored by intracerebral microdialysis," *J. Neurochem.*, 43(5):1369–1374 (1984).

Olney, J. W., "Inciting excitotoxic cytocide among central neurons," *Adv. Exp. Med. Biol.*, 203:631–645 (1986).

Sattayasai, et al., "Morphology of quisqualate–induced neurotoxicity in the chicken retina," *Invest. Ophthalmol. Vis. Sci.*, 28:106–117 (1987).

Tung, et al., "A quantitative analysis of the effects of excitatory neurotoxins on retinal ganglion cells in the chick," *Visual Neurosci.*, 4:217–223 (1990).

Sisk, et al., "histological changes in the inner retina of albino rats following intravitreal injetion of monosodium L–glutamate," *Graefe's Arch. Clin. Exp. Ophthalmol.*, 223:250–258 (1985).

Siliprandi, et al., "N–methyl–D–aspartate–induced neurotoxicity in the adult rat retina," *Visual Neurosci.*, 8:567–573 (1992).

Reif–Lehrer, et al., "Effects of monosodium glutamate on chick embryo retina in culture," *Invest. Ophthalmol. Vis. Sci.*, 14(2):114–124 (1975).

Blanks, J. C., "Effects of monosodium glutamate on the isolated retina of the chick embryo as a function of age: A morphological study," *Exp. Eye. Res.*, 35:105–124 (1981).

Olney, et al., "The role of specific ions in glutamate neurotoxicity," *Neurosci. Lett.*, 65:65–71 (1986).

Olney, et al., "The anti–excitotoxic effects of certain anesthetics, analgesics and sedative–hypnotics," *Neurosci. Lett.*, 68:29–34 (1986).

Price, et al., "CNQX potently and selectively blocks kainate excitotoxicity in the chick embryo retina," *Soc. Neurosci. Abst.*, 14:418 (1988).

Caprioli, et al., "Large retinal ganglion cells are more susceptible to excitotoxic and hypoxic injury than small cells," *Invest. Ophthalmol. Vis. Sci.*, 34(Suppl):1429 (1993).

Cummins, et al., "Electrophysiology of cultured retinal ganglion cells to investigate basic mechanics of damage," *Glaucoma Update IV*, 59–65 (1991).

Sucher, et al., "N–methyl–D–aspartate antagonists prevent kainate neurotoxicity in rat retinal ganglion cells in vitro," *J. Neurosci.*, 11(4):966–971 (1991).

Lipton, S.A., "Prospects for clinically tolerated NMDA antagonists: open–channel blockers and alternative redox states of nitric oxide," *TINS*,16(12):527–532 (1993).

Yoon, Y. H., and Marmor, M. F., "Dextromethorphan Protects Retina Against Ischemic Injury In Vivo," *Arch. Ophthalmol.*, 107:409–411 (1989); and.

Gupta, L. Y., and Marmor, M. F., "Mannitol, Dextromethorphan, and Catalase Minimize Ischemic Damage to Retinal Pigment Epithelium and Retina," *Arch. Ophthalmol.*, 111:384–388 (1993).

*Primary Examiner*—Zohreh Fay
*Attorney, Agent, or Firm*—Sally Yeager

[57] ABSTRACT

The use of polyamine site antagonists in treating ischemic disorders of the retina and optic nerve head are disclosed. Especially preferred are certain 1-phenyl-2-piperidinoalkanol derivatives, such as eliprodil and ifenprodil.

8 Claims, 1 Drawing Sheet

TREATMENT OF ISCHEMIC DISORDERS OF THE RETINA AND OPTIC NERVE HEAD

This application is a continuation of application Ser. No. 08/582,003, filed Jan. 2, 1996 now abandoned.

The present invention relates generally to the field of ophthalmology. In particular, the invention relates to the use of eliprodil and related agents that prevent or attenuate ischenic mediated neuronal injury and hence are useful for treating ischemia or hypoxia of the retina or optic nerve head in mammalian subjects.

BACKGROUND OF THE INVENTION

It is known that oxygen debt within the tissues supplied by the retinal artery is associated with changes to the inner retina Acute changes include swelling of the inner nuclear, inner plexiform, and ganglion cell layers. Typically, in a matter of days pyknotic nuclei are observed, which is followed by loss of ganglion cells and a thinning of the inner retina. Many of the histological changes observed in the inner retina following hypoxia were elucidated using the chick embryo retina preparation. David used this model to show that when subjected to anoxia, morphological changes occurred that were similar to the toxic effects of glutamate or potassium administration David, P., et al., "Involvement of excitatory neurotansmitters in the damage produced in chick embryo retinas by anoxia and extracellular high potassium," *Exp. Eye Res.* 46: 65762, 1988). Immunocytochemical and electrophysiological studies have unequivocally proven that glutamate is the major excitatory neurotansmitter in the retina as well as most other regions in the central nervous system (Massey, S., "Cell types using glutamate as a neurotansmitter in the verebrate retina," *Progress in Retinal Research*, Volume 9, edited by N. N. Osborne and G. J. Chader, Oxford: Pergammon Press, 399–425, 1990; Miller, R. F. and M. M. Slaughter, "Excitatory amino acid receptors in the vertebrate retina," Retinal Transmitters and Modulators, Volume II, edited by W. W. Morgan. Boca Raton: CRC Press, Inc. 123–160, 1985). Under normal conditions neuronal release of glutamate is presynaptic and mediates an excitatory response on postsynaptic excitatory amino acid (EAA) receptors. Dissociation from these receptors as well as uptake into presynaptic neurons and/or glial cells is very rapid. Under certain conditions glutamate release can be excessive and uptake mechanisms compromised. In the central nervous system it has been demonstrated that brief periods of ischemia can rapidly increase glutamate levels. Beneviste demonstrated increases in glutamate in the adult rat brain within minutes of global cerebral ischemia (Beneviste, H. et al., "Elevation of the extracellular concentrations of glutamate and aspartate in rat hippocampus during transient cerebral ischemia monitored by intracerebral microdialysis," *J. Neurochem.* 43(5): 1369–1374, 1984.).

Excessive EAA stimulation, referred to as excitotoxicity, can result in neuronal injury (Olney, J. W., "Inciting excitotoxic cytocide among central neurons," *Adv. Exp. Med Biol.* 203:631–645, 1986). The process of excitotoxicity has been extensively studied in the retina Such toxicity to the inner retina has been observed following intravitreal injection of EAAs, following application of EAAs to the isolated animal retina, or from exogenously applied glutamate to retinal ganglion cells in culture. See generally, Sattayasai, et al., "Morphology of quisqualate-induced neurotoxicity in the chicken retina," *Invest. Ophthalmol. Vis. Sci.,* 28:106–117 (1987); Tung, et al., "A quantitative analysis of the effects of excitatory neurotoxins on retinal ganglion cells in the chick," *Visual Neurosci.,* 4:217–223 (1990); Sisk, et al., "Histological changes in the inner retina of albino rats following intravitreal injection of monosodium L-glutamate," *Graefe's Arch. Clin. Exp. Ophthamol.,* 223:250–258 (1985); Siliprandi, et al., "N-methyl-D-aspartate-induced neurotoxicity in the adult rat retina," *Visual Neurosci.,* 8:567–573 (1992); Reif-Lehrer, et al., "Effects of monosodium glutamate on chick embryo retina in culture," *Invest. Ophthalmol. Vis. Sci.,* 14(2):114–124 (1975); Blanks, J. C., "Effects of monosodium glutamate on the isolated retina of the chick embryo as a function of age: A morphological study," *Exp. Eye Res.,* 32:105–124 (1981); Olney, et al., "The role of specific ions in glutamate neurotoxicity," *Neurosci. Lett.,* 65:65–71 (1986); Olney, et al., "The anti-excitotoxic effects of certain anesthetics, analgesics and sedative-hypnotics,", *Neurosci. Lett.* 68:29–34 (1986); Price, et al., "CNQX potently and selectively blocks kainate excitotoxicity in the chick embryo retina," *Soc. Neurosci. Abst.,* 14:418 (1988); David, et al., "Involvement of excitatory neurotansmitters in the damage produced in chick embryo retinas by anoxia and extracellular high potassium," *Exp. Eye Res.,* 46:657–662 (1988); Caprioli, et al., "Large retinal ganglion cells are more susceptible to excitotoxic and hypoxic injury than small cells," *Invest. Ophthalmol. Vis. Sci.,* 34(Suppl):1429 (1993); Cummins, et al., "Electrophysiology of cultured retinal ganglion cells to investigate basic mechanics of damage," *Glaucoma Update IV,* 59–65 (1991); and Sucher, et al., "N-methyl-D-aspartate antagonists prevent kainate neurotoxicity in rat retinal ganglion cells in vitro," *J. Neurosci.,* 11(4):966–971 (1991).

EAA receptors have been characterized as metabotropic or ionotropic. Activation of a metabotropic receptor affects cellular processes via G-proteins; whereas ionotropic receptors affect the tanslocation of mono- and divalent cations across the cell membrane. There are at least free ionotropic receptors that have been named for the agonist that preferentially stimulates the receptor. These receptors have been classified as: N-methyl-D-aspartate (NMDA); kainate; and 2-amino-3-(3-hydroxy-5- methylisoxazol- 4-yl) propanoic acid (AMPA) receptors. These EAA receptors are differentially distributed in specific cells in the retina (See, for example, Massey, S., "Cell types using glutamate as a neurotransmitter in the vertebrate retina," N. N. Osborne and G. J. Chader (Eds.) *Progress in Retinal Research,* Ch 9, Pergammon Press: Oxford, 399–425 (1990); and Miller, et al., "Excitatory amino acid receptors in the vertebrate retina," *Retinal Transmitters and Modulators: Models for the Brain,* (W. W. Morgan, Ed.) CRC Press, Inc., Boca Raton, II: 123–160 (1985).) The localization of such receptors accounts for the pathologies associated with ischemia of the retina or optic nerve head. For example, death of the retinal ganglion cell induced by kainate has to a large part been attributed to the NMDA receptor. (See, for example, Sucher, et al., "N-methyl-D-aspartate antagonists prevent kainate neurotoxicity in retinal ganglion cells in vitro," *J. Neurosci.,* 11(4):966–971 (1991).).

SUMMARY OF THE INVENTION

The present invention is directed to methods for treating ischemic disorders of the eye with polyamine site antagonists.

DETAILED DESCRIPTION OF THE INVENTION

Figure 1:
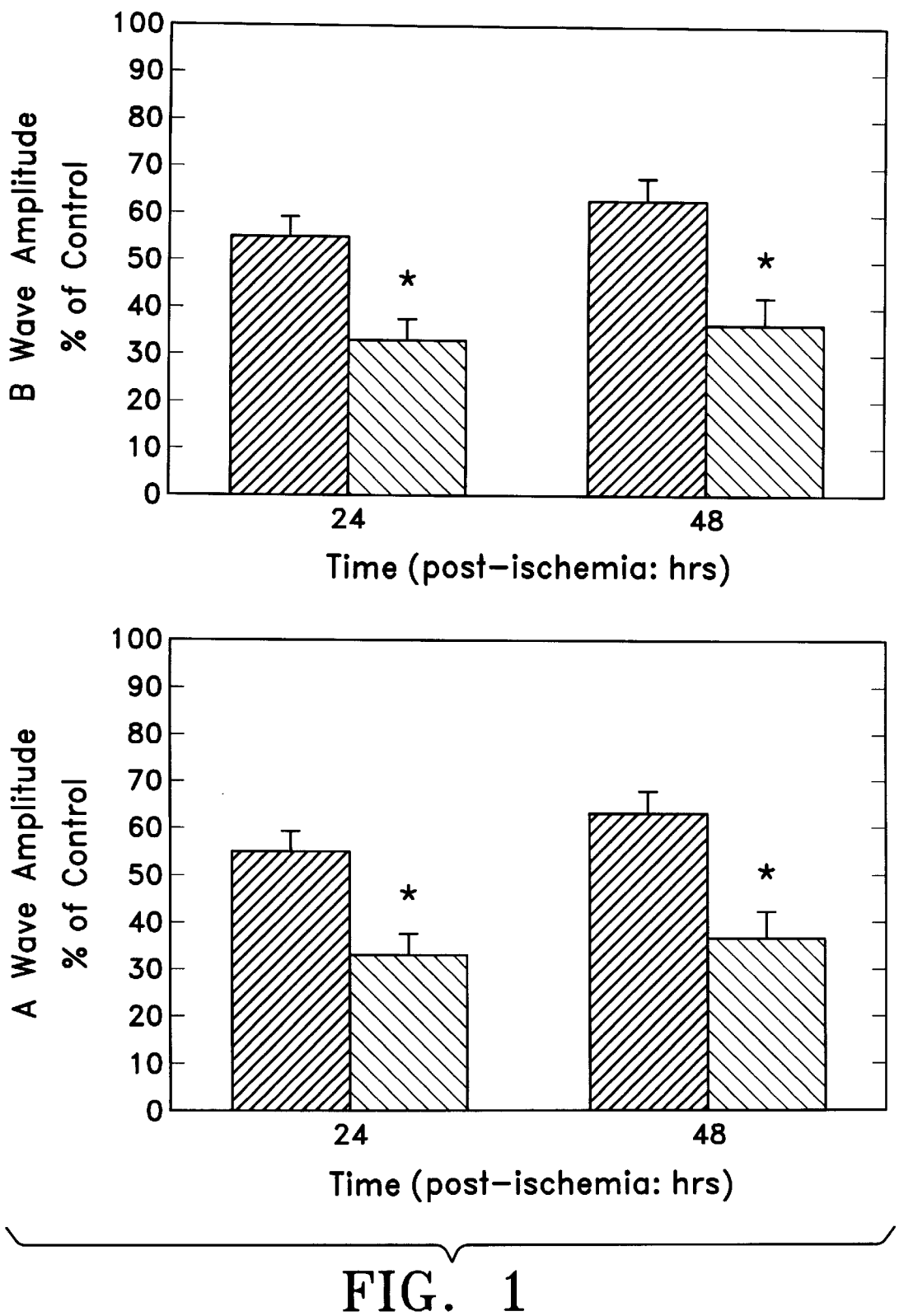
FIGURE 1 shows the effect of eliprodil on the restoration of the electroretinogram following ischemic challenge in the pigmented rabbit.

Polyamine site antagonists are useful in treating ischemic disorders of the mammalian, particularly human, retina (e.g. branch and central vein/artery occlusion) or optic nerve head (e.g. anterior ischemic optic neuropathy).

Unlike other NMDA antagonists, polyamine site antagonists, such as eliprodil, partition across the blood-brain barrier and produce their actions at a modulatory site without side-effects typical of non-competitive antagonists. (See, for example, Lipton, S. A., "Prospects for clinically tolerated NMDA antagonists: open-channel blockers and alternative redox states of nitric oxide," *TINS*, 16(12): 527–532 (1993).)

Particularly preferred polyamine site antagonists are certain 1-phenyl-2-piperidino-alkanol derivatives of formula (I), below:

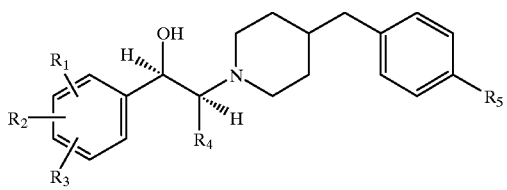

wherein:
- $R_1$ represents a hydrogen atom a halogen atom, a trifluoromethyl group, an alkyl group having from 1 to 4 carbon atoms, a hydroxyl group, an alkoxy group having from 1 to 4 carbon atoms, a benzyloxy group, an alkanoyloxy group having from 1 to 16 carbon atoms or a benzoyloxy group, or, when $R_2$ represents a hydroxyl or methoxy group in the 4position and $R_3$ represents a hydrogen atom, $R_1$ may also represent a hydroxymethyl group, a carbamoyl group or an alkoxycarbonyl group having from 1 to 4 carbon atoms in the alkoxy part $R_2$ represents a hydrogen atom, a halogen atom, an alkyl group having from 1 to 4 carbon atoms, a hydroxyl group or an alkoxy group having from 1 to 4 carbon atoms,
- $R_3$ represents a hydrogen atom or an alkyl group having from 1 to 4 carbon atoms,
- $R_4$ represents an alkyl group having from 1 to 4 carbon atoms, in which case the compounds are in the (±)-erythro form, or, when $R_3$ represents a hydrogen atom, $R_4$ may also represent a hydrogen atom, and $R_5$ represents a hydrogen atom, a halogen atom, an alkyl group having from 1 to 4 carbon atoms, an alkoxy group having from 1 to 4 carbon atoms or a set of three methoxy groups in the 3-, 4- and 5-positions of the benzyl radical, and pharmaceutically acceptable acid addition salts thereof.

The compounds of formula (I) above are described in U.S. Pat. No. 4,690,931 (Wick et al.); however, there is no mention in that patent of ophthalmic indications for such compounds. Wick, et al. also describe methods for synthesizing such compounds. The entire contents of U.S. Pat. No. 4,690,931 are incorporated herein by reference.

The most preferred compounds are: 2-[4-(4-fluorobenzyl)-piperidino]-1-(4-chlorophenyl)-ethanol, also known as eliprodil; 2-(4-benzylpiperidino)1-(4-hydroxyphenyl)-propanol, also known as ifenprodil; or a pharmaceutically acceptable salt thereof. The structures of eliprodil and ifenprodil are shown below.

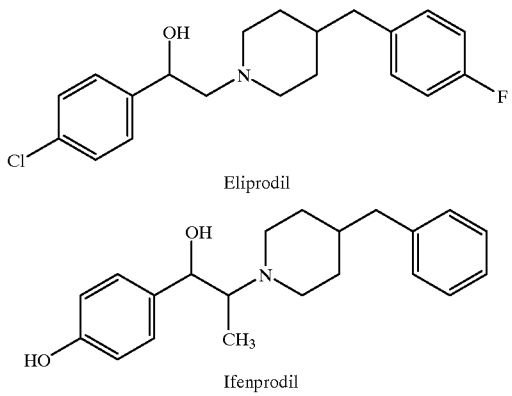

In general, the polyamine site antagonists useful in the present invention will be administered orally. Daily dosage of these compounds will range between about 0.1 and about 500 milligrams (mg), preferably between about 5 and about 100 mg. Local administration of these compounds will range between about 0.1 and about 500 mg, preferably between about 5 and about 100 mg. An aqueous composition will generally contain between about 0.1 and about 10 percent by weight (wt %) of the active, preferably between about 1 and about 5 wt %.

The following example is presented to illustrate further various aspects of the present invention, but is not intended to limit the scope of the invention in any respect.

EXAMPLE

Studies were conducted to evaluate the effect of Eliprodil on the recovery of the ERG (electroretinogram) following an ischemic challenge in the pigmented rabbit. This experimental paradigm is thought to be a good model for evaluating the possible beneficial effects of therapeutic agents on retinal damage caused by interruption of blood flow (Yoon, Y. H., and Marmor, M. F., "Dextromethorphan Protects Retina Against Ischemic Injury In Vivo", *Arch. Ophthalmol.* 107:409–411(1989); Gupta, L. Y., and Marmor, M. F., "Mannitol, Dextromethorphan, and Catalase Minimize Ischernic Damage to Retinal Pigment Epithelium and Retina", *Arch. Ophthalmol.* 111:384–388(1993). Ischemia was produced by mechanically elevating intraocular pressure above systemic blood pressure for 65 minutes. Just prior to and during the ischemic period, all rabbits were put into a surgical plane of anesthesia by administering sodium pentobarbital. Ischemia was confirmed by a cessation of A and B wave activity (<15 ($\mu$V). One hour prior to ischemia, rabbits were administered intravenously 3 mg/kg of Eliprodil. 10 mg/kg Eliprodil was given intraperitoneally at 0, 12, 24 and 36 hours following the ischemic period. ERG recordings were made prior to ischemia and at 24 and 48 hours post-ischemia. Results of this experiment are presented (FIG. 1) as a function of percent of baseline (pre-ischemia measurement). Values are mean±SEK- N=5 vehicle; N=6 for eliprodil. Baseline B wave amplitude=456+ 32 and 441+28 $\mu$V for eliprodil and vehicle groups. Baseline A wave amplitude=−143+8 and −130+3 $\mu$V for eliprodil and vehicle.

Panel A shows the effect of Eliprodil on B wave amplitude compared to vehicle treated animals. B wave amplitude is thought to be a composite of Müuller's cell and Bipolar cell activity. Drug treatment resulted in a 70.7% and 77.9% increase (p<0.05) over vehicle treated amplitudes at 24 and 48 hours post ischemia, respectively. In panel B, the functionality of the outer retina was evaluated through measurement of A wave amplitude. The 24 hour increase in A wave amplitude by Eliprodil treated rabbits (109% increase above vehicle) was proportionally greater than that seen in the B wave amplitude at this period.

Thus in this experiment, Eliprodil clearly improved the functional condition of the retina following an ischemic insult.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

We claim:

1. A method for treating ischemic disorders of the eye which comprises, administering to an affected person a pharmaceutically effective amount of eliprodil.

2. The method of claim 1, wherein the affected person is administered between about 0.1 and about 500 mg of eliprodil on a daily basis.

3. The method of claim 2, wherein the affected person is administered between about 5 and about 100 mg of eliprodil on a daily basis.

4. A composition for treating ischemic disorders of the eye comprising a pharmaceutically effective amount of eliprodil.

5. The method of claim 1 wherein the ischemic disorder is in the retina.

6. The method of claim 5 wherein the ischemic disorder is selected from the group consisting of branch vein/artery occlusion and central vein/artery occlusion.

7. The method of claim 1 wherein the ischemic disorder is in the optic nerve head.

8. The method of claim 7 wherein the ischemic disorder is anterior ischemic optic neuropathy.

* * * * *